United States Patent
Chen et al.

(10) Patent No.: US 11,202,797 B2
(45) Date of Patent: Dec. 21, 2021

(54) MIXTURE OF FUCOSYLATED CHONDROITIN SULFATE OLIGOSACCHARIDES AND METHOD FOR RAPIDLY PRODUCING THE SAME

(71) Applicant: ZHEJIANG UNIVERSITY, Hangzhou (CN)

(72) Inventors: Shiguo Chen, Hangzhou (CN); Lufeng Yan, Hangzhou (CN); Danli Wang, Hangzhou (CN); Junhui Li, Hangzhou (CN); Xingqian Ye, Hangzhou (CN); Donghong Liu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/762,147

(22) PCT Filed: Jul. 11, 2018

(86) PCT No.: PCT/CN2018/095211
§ 371 (c)(1),
(2) Date: May 7, 2020

(87) PCT Pub. No.: WO2020/010534
PCT Pub. Date: Jan. 16, 2020

(65) Prior Publication Data
US 2020/0261493 A1    Aug. 20, 2020

(51) Int. Cl.
*A61K 31/737* (2006.01)
*B01D 61/14* (2006.01)
*C08B 37/00* (2006.01)
*A61P 7/02* (2006.01)
*A61P 9/10* (2006.01)

(52) U.S. Cl.
CPC .............. *A61K 31/737* (2013.01); *A61P 7/02* (2018.01); *A61P 9/10* (2018.01); *B01D 61/142* (2013.01); *C08B 37/0069* (2013.01)

(58) Field of Classification Search
CPC .......................... A61K 31/737; C08B 37/0069
See application file for complete search history.

(56) References Cited

FOREIGN PATENT DOCUMENTS

| CN | 102329397 | * | 1/2012 |
| CN | 103214591 Y | | 7/2013 |
| CN | 104130334 | * | 11/2014 |

OTHER PUBLICATIONS

Zhao, L. et al "Structure and anticoagulant activity of fucosylated glycosaminoglycan . . . " Carbohyd. Polym., vol. 98, pp. 1514-1523. (Year: 2013).*
Wu, N. et al "Depolymerization of fucosylated chondroitin sulfate . . . " Carbohyd. Polym., vol. 93, pp. 604-614.. (Year: 2013).*
Yan, L. et al "Molecular size is important of the safety and selective inhibition . . . " Carbohyd. Polym., vol. 178, pp. 180-189. (Year: 2017).*
International Search Report (PCT/CN2018/095211); dated Dec. 9, 2019.
Structure and Bioactivity Analysis of Fucosylated Chondrointin Sulfate from Pearsonothuria Graeffei and its Oligosaccharides (Chinese Master's Theses Full-text Database),(Engineering Science & Technology I), No. 7, Jul. 15, 2014, ISSN: 1674-0246.

* cited by examiner

*Primary Examiner* — Leigh C Maier
(74) *Attorney, Agent, or Firm* — W&G Law Group (57) ABSTRACT

The present invention discloses a mixture of fucosylated chondroitin sulfate oligosaccharides having an average molecular weight between 2700 Da and 3600 Da, in which 90% of total components has a molecular weight between 1800 Da and 5400 Da. The mixture of fucosylated chondroitin sulfate oligosaccharide of the present invention has very low anti-FIIa factor activity, very low anti-FXa factor activity, very high anti-FXase factor activity, i.e., having a significant activity in selectively inhibiting intrinsic FXase, and a significant antithrombotic activity and no risk of bleeding and hypotension that are proved through animal experiments. The present invention also discloses a method for rapidly producing fucosylated chondroitin sulfate oligosaccharides by using sea cucumber as raw material, and the method includes: intercepting and concentrating crude polysaccharide with a membrane, deacetylation with hydrazine, pyrolysis with nitrous acid, reduction with sodium borohydride, membrane separation, etc., achieving rapid preparation and high yield.

8 Claims, 5 Drawing Sheets

MIXTURE OF FUCOSYLATED CHONDROITIN SULFATE OLIGOSACCHARIDES AND METHOD FOR RAPIDLY PRODUCING THE SAME

CROSS-REFERENCE TO RELATED APPLICATIONS

This is the United States national phase of International Patent Application No. PCT/CN2018/095211, filed on Jul. 11, 2018, the entire contents of which are incorporated herein by reference.

TECHNICAL FIELD

The present invention relates to a mixture of fucosylated chondroitin sulfate oligosaccharides and a producing method thereof, and particularly, to a mixture of fucosylated chondroitin sulfate oligosaccharides having a controlled molecular weight distribution, and a method for rapidly producing the mixture of fucosylated chondroitin sulfate oligosaccharides.

BACKGROUND

Fucosylated chondroitin sulfate is an acidic mucopolysaccharide derived from the body wall of sea cucumber, which has a chondroitin sulfate main chain and different sulfated fucose branches, and has significant anticoagulant and antithrombotic physiological functions. However, fucosylated chondroitin sulfate polysaccharide has side effects such as promoting platelet aggregation and causing hypotension, which limit it to be developed as a clinical anticoagulant drug. It is reported that degradation of fucosylated chondroitin sulfate polysaccharide can retain the anticoagulant activity and reduce side effects. However, a safe and effective molecular weight range of fucosylated chondroitin sulfate oligosaccharides and products thereof have not been reported yet.

Therefore, it is of great significance to determine a safe and effective molecular weight range of the fucosylated chondroitin sulfate oligosaccharides and products thereof. It is urgent in the field to obtain a product of fucosylated chondroitin sulfate oligosaccharides having a controlled molecular weight distribution, a strictly controlled quality, significant anticoagulant and antithrombotic activities, and no bleeding and hypotension side effects.

The polysaccharide in the body wall of sea cucumber mainly include fucosylated chondroitin sulfate (FCS) and fucoidan, which are usually separated and purified with the ion exchange method at present, so as to obtain the fucosylated chondroitin sulfate with high purity, and then the fucosylated chondroitin sulfate is degraded through free radical oxidation. Such a separation and purification method of polysaccharide is time-consuming, labor-intensive and costly. In the meantime, although the degradation through free radical oxidation has high efficiency, the free radicals may attack any glycosidic bond, and thus it is difficult to control the structure of product.

Therefore, it is of great significance to develop a method for rapidly producing fucosylated chondroitin sulfate oligosaccharides having a safe and effective molecular weight range by using cheap sea cucumber as a raw material.

SUMMARY

A purpose of the present invention is to provide a mixture of fucosylated chondroitin sulfate oligosaccharides having a controlled molecular weight distribution, strict controlled quality, significant anticoagulant and antithrombotic activities, and no bleeding and hypotension side effects.

Another purpose of the present invention is to provide a method for rapidly producing the mixture of fucosylated chondroitin sulfate oligosaccharides by hydrazine-nitrite combined selective pyrolysis of membrane-separated and enriched crude sea cucumber polysaccharide and further membrane separation.

Technical solutions adopted by the present invention are as follows: a mixture of fucosylated chondroitin sulfate oligosaccharides having the following characteristics:

(1) an average molecular weight is smaller than 5400 Da;

(2) a proportion of components having a molecular weight smaller than 5400 Da is not less than 60%;

(3) the mixture of fucosylated chondroitin sulfate oligosaccharides prolongs APTT, i.e., having a significant effect in inhibiting the intrinsic coagulation pathway, but does not prolong TT, i.e., having no significant effect in inhibiting the common coagulation pathway;

(4) an anti-FXase factor activity is not lower than 50 IU/mg;

(5) an anti-FIIa factor activity is not higher than 1 IU/mg; and (6) an anti-FXa factor activity is not higher than 5 IU/mg.

Further, the mixture of fucosylated chondroitin sulfate oligosaccharides has the following characteristics:

(1) the average molecular weight is between 2700 Da and 3600 Da;

(2) 90% of total components has a molecular weight between 1800 Da and 5400 Da, and is trisaccharide-repeating units of varying degrees;

(3) the anti-FXase factor activity is not lower than 60 IU/mg;

(4) an inhibition rate of deep vein thrombosis in rats at a dose of 10 mg/kg is not smaller than 80%, and an inhibition rate of deep vein thrombosis in rats at a dose of 5 mg/kg is not smaller than 50%; and (5) the mixture of fucosylated chondroitin sulfate oligosaccharides has no risk of bleeding and hypotension.

A method for rapidly producing fucosylated chondroitin sulfate oligosaccharides has the following steps:

(1) pulverizing sea cucumber, mixing the pulverized sea cucumber, protease and a buffer solution having a pH of 5-8 according to a solid-liquid ratio of 1 g:(0.05-0.15) g:(10-30) mL for enzymolysis, and then boiling to inactivate enzyme, so as to obtain an enzymatic hydrolysate;

(2) intercepting the enzymatic hydrolysate obtained in step (1) with an ultrafiltration membrane to obtain a crude polysaccharide concentrate solution, subjecting the crude polysaccharide concentrate solution to repeated diluting with water and concentrating by intercepting with an ultrafiltration membrane until a permeate is colorless, and then lyophilizing the concentrate solution to obtain crude polysaccharide;

(3) uniformly mixing the crude polysaccharide obtained in step (2) and hydrazine hydrate at a ratio of 1 g:(5-20) mL, adding catalyst for catalyzing a deacetylation effect of the hydrazine hydrate on fucosylated chondroitin sulfate in the crude polysaccharide, reacting at 60-105° C. for 6-24 h, to obtain a reaction solution;

(4) adding absolute ethanol, adding saturated saline dropwise until the crude polysaccharide precipitates, harvesting a precipitate after centrifuging, and re-dissolving the precipitate into water to obtain a crude polysaccharide solution;

(5) repeating step (4), and transferring a crude polysaccharide solution obtained after repeating step (4) more than twice to a dialysis bag to remove residual ethanol and hydrazine by dialysis;

(6) centrifuging the dialyzed crude polysaccharide solution in step (5) to separate pigment impurities from polysaccharide, lyophilizing a supernatant containing the polysaccharide, and then dissolving the lyophilized polysaccharide in pure water to obtain a polysaccharide solution for later use;

(7) mixing an ice-bathed nitrous acid solution with the polysaccharide solution obtained in step (6), reacting in an ice bath for 10-60 min, then adding a sodium hydroxide solution until the reaction solution is neutral to terminate the reaction, and adding a sodium borohydride solution for reduction; and (8) transferring a product obtained in step (7) to a dialysis bag to remove residual salts by dialysis, and then intercepting fucosylated chondroitin sulfate oligosaccharides with an ultrafiltration membrane, to obtain components having a molecular weight smaller than 6000 Da.

Further, in step (1), the protease is papain, and the buffer solution is an acetic acid-sodium acetate buffer solution having a concentration of 0.05-0.15 mol/L, and the solid-liquid ratio is 1 g:(0.08-0.12) g:(15-25) mL, a temperature of the enzymolysis is 50-70° C., and a duration of the enzymolysis is 12-24 h.

Further, the ultrafiltration membrane used in step (2) has a pore size of 10-50 kDa.

Further, in step (3), the crude polysaccharide and the hydrazine hydrate are mixed at a ratio of 1 g:(8-12) mL, the added catalyst is hydrazine sulfate or hydrazine hydrochloride, a reacting temperature is 90-105° C., and a reacting duration is 8-18 h.

Further, the dialysis bag used in step (5) has a molecular pore size of 500-3500 Da.

Further, in step (6), a rotation speed of the centrifuging is 8000 rpm or greater.

Further, in step (7), the nitrous acid solution is prepared by mixing a 5.5 mol/L sodium nitrite solution with 0.5 mol/L sulfuric acid in a volume ratio of 5:(2-4), the sodium hydroxide solution has a concentration of 0.5 mol/L, the sodium borohydride solution has a concentration of 150 mg/mL, and the reduction is performed at 50° C. for 2 h.

Further, in step (8), the dialysis bag has a pore size of 100-500 Da, the fucosylated chondroitin sulfate oligosaccharides were intercepted with an ultrafiltration membrane having a pore size of 5 kDa and an ultrafiltration membrane having a pore size of 10 kDa.

Further, the molecular weight is concentrated between 1800 Da and 5400 Da, the anti-FIIa factor activity and anti-FXa factor activity are very low, and the anti-FXase factor activity is very high. That is, the mixture of fucosylated chondroitin sulfate oligosaccharides has a significant activity of selectively inhibiting intrinsic FXase, and a significant antithrombotic activity and no risk of bleeding and hypotension that are proved through animal experiments.

Compared with the existing fucosylated chondroitin sulfate oligosaccharides, the fucosylated chondroitin sulfate oligosaccharides according to the present invention has the following advantages:

(1) the molecular weight distribution is more concentrated. In a preferred technical solution, an average molecular weight is between 2700 Da and 3600 Da, 90% of total components has a molecular weight between 1800 Da to 5400 Da, and is trisaccharide-repeating units of varying degrees, so that the quality is strictly controlled and the product quality is more stable.

(2) the APTT is prolonged, i.e., the effect in inhibiting the intrinsic coagulation pathway is significant, but the TT is not prolonged, i.e., the effect in inhibiting the common coagulation pathway is not significant, indicating an activity in selectively inhibiting the coagulation factors.

(3) the anti-FIIa factor activity and the anti-FXa factor activity are very low, and particularly, the anti-FIIa factor activity is extremely low, but the anti-FXase factor activity is significant, which further indicates a significant activity in selectively inhibiting intrinsic FXase. The fucosylated chondroitin sulfate oligosaccharides having a molecular weight lower than 1800 Da will completely lose the anticoagulant and antithrombotic activities, and the fucosylated chondroitin sulfate oligosaccharides having a molecular weight greater than 7200 Da will have side effects of bleeding and hypotension. Components having a molecular weight between 1800 Da and 5400 Da account for 90% of total components of the fucosylated chondroitin sulfate oligosaccharides according to the present invention and are selective anticoagulant and antithrombotic effective molecules, and the animal experiments show no side effects of bleeding and hypotension.

(4) the method of the present invention has the characteristics of high efficiency and high yield. The conventional method for producing fucosylated chondroitin sulfate oligosaccharides from sea cucumber raw materials usually takes nearly one month for extraction, separation and purification, and unselective degradation of fucosylated chondroitin sulfate polysaccharides. In addition, it is difficult to control the quality of the obtained product and the yield is low. In a preferred technical solution of the present invention, it takes only one week to fully utilize the fucosylated chondroitin sulfate polysaccharides in the raw material for degradation, and the oligosaccharides having a molecular weight distribution concentrated in a safe and effective range are obtained with a high yield.

DESCRIPTION OF EMBODIMENTS

Hydrazine-Nitrite Combined Pyrolysis of Fucosylated Chondroitin Sulfate from Natural Sources The sea cucumbers are crushed, proteins are enzymatically hydrolyzed to release polysaccharides, and two crude polysaccharides, fucosylated chondroitin sulfate and fucoidan, are enriched by ultrafiltration, and the crude polysaccharides are lyophilized and treated with hydrazine hydrate to partially deacetylate the fucosylated chondroitin sulfate and promote separation of pigments from mucopolysaccharide. Then a polysaccharide supernatant is obtained by centrifugation and lyophilized. The obtained mixed polysaccharides are reacted with nitrous acid, so that nitrous acid selectively attacks the exposed amino groups on the carbohydrate chains. In this way, the fucosylated chondroitin sulfate is degraded into repeated trisaccharide unit fragments of different polymerization degrees, while the molecular weight of fucoidan is not affected and is concentrated at 300 kDa, and fucosylated chondroitin sulfate oligosaccharides having a molecular weight concentrated at 1800 Da (6 oligomers6-mer) to 5400 Da (18 oligomers18-mer) were obtained by intercepting with an ultrafiltration membrane.

Figure 7:
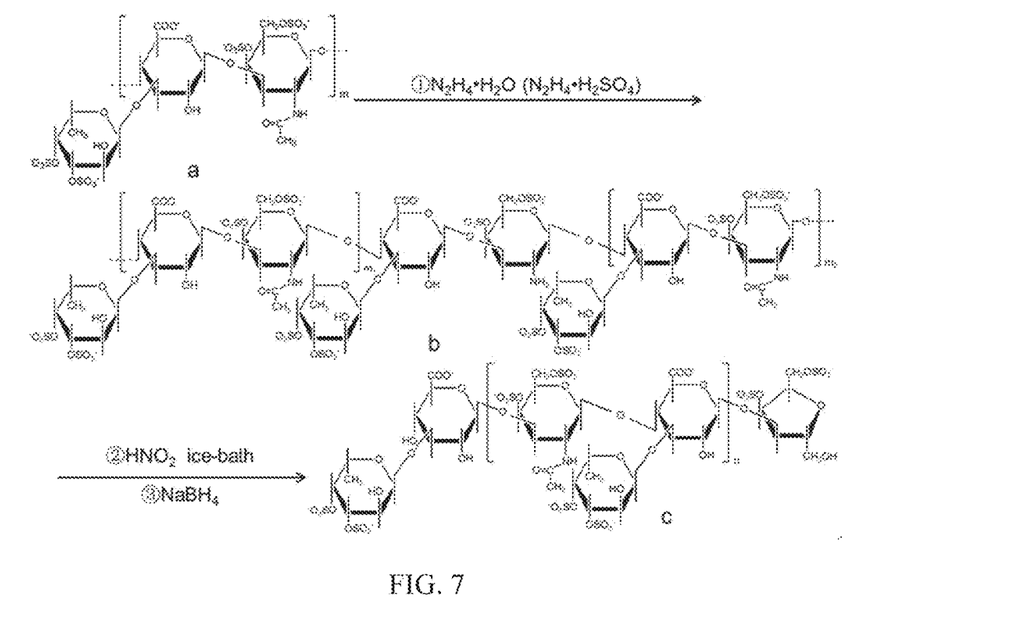
FIG. 7 is a schematic diagram of selective degradation of fucosylated chondroitin sulfate.

A selective degradation of fucosylated chondroitin sulfate is illustrated in FIG. 7, where a: fucosylated chondroitin sulfate polysaccharide; b: partially deacetylated fucosylated chondroitin sulfate; and c: a mixture of fucosylated chondroitin sulfate oligosaccharides.

The present invention is further described in combination with the specific examples.

Example 1

Figure 1:
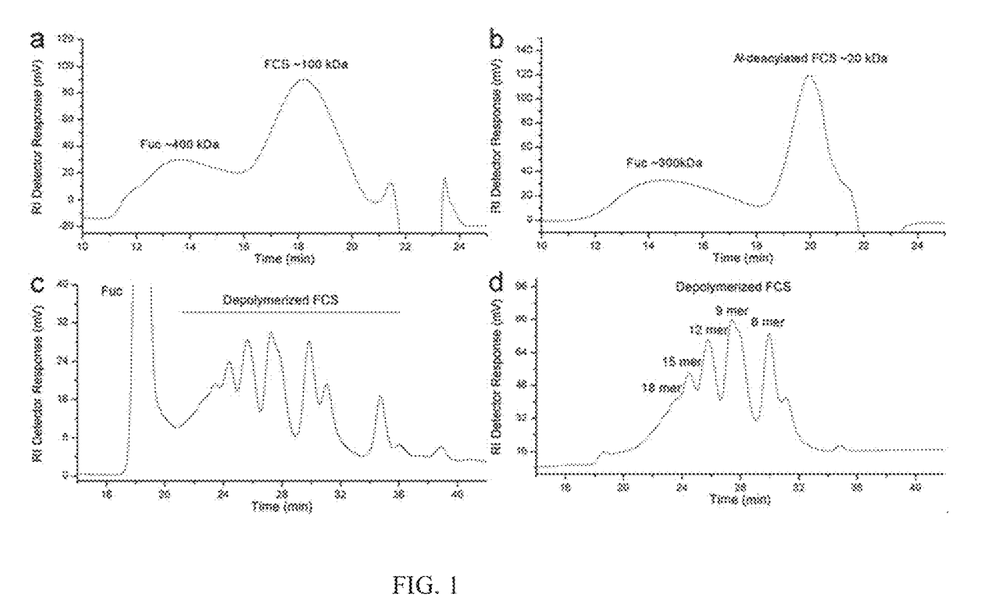
FIG. 1 illustrates schematic diagrams of molecular weight distribution of samples at different stages during producing fucosylated chondroitin sulfate oligosaccharides: a. crude polysaccharides of sea cucumber, containing fucoidan and fucosylated chondroitin sulfate (FCS); b. crude polysaccharides after hydrazine treatment, containing fucoidan and partially deacetylated fucosylated chondroitin sulfate (N-deacylated FCS); c. a degraded sample, containing fucoidan and depolymerized fucosylated chondroitin sulfate (depolymerized FCS); d. fucosylated chondroitin sulfate oligosaccharides intercepted by ultrafiltration membrane, mainly containing 6 oligomers to 18 oligomers (6-18 mer).

(1) 100 g of dry powder of *Pearsonothuria graeffei* was uniformly mixed with 3 L of acetic acid-sodium acetate buffer solution (0.05 mol/L; pH 5), and then the temperature was raised to 50° C., 15 g of papain was added and mixed uniformly to perform enzymolysis for 12 h, and then the mixture was boiled to inactive the enzyme;

(2) The crude polysaccharide was enriched by using a 10 kDa ultrafiltration membrane, washed with pure water until the permeate was colorless, and then lyophilized. The molecular weight and the molecular weight distribution were measured, and the results are shown in FIG. 1-a;

(3) 5 g of the crude polysaccharide was sufficiently dissolved in 100 mL of hydrazine hydrate and 100 mg of hydrazine sulfate was added to react at 105° C. for 6 h, so as to obtain a reaction solution;

(4) Absolute ethanol and saturated saline were added, a precipitate was obtained through centrifugation, and the precipitate was dissolved in water;

(5) After repeating the above operation 3 times, the precipitate was dissolved in water and dialyzed against water with a 3500 Da dialysis bag for 48 h;

(6) The dialyzed crude polysaccharide solution was appropriately concentrated and centrifuged at 8000 rpm, the supernatant was lyophilized, and then the molecular weight and the molecular weight distribution were measured. The results are shown in FIG. 1-b. 1 g of the lyophilized polysaccharide was taken and dissolved in pure water to obtain a solution (40 mg/mL) which was then kept in an ice bath for later use;

(7) 5.5 mol/L sodium nitrite solution and 0.5 mol/L sulfuric acid were mixed in a volume ratio of 5:2 to obtain a nitrous acid solution which was then kept in the ice bath, 50 mL of the nitrous acid solution was then taken, mixed with 25 mL of the polysaccharide solution and reacted in an ice bath for 60 min, then 0.5 mol/L sodium hydroxide solution was added until the reaction solution is neutral to terminate the reaction, and then 3 mL of 150 mg/mL sodium borohydride solution was rapidly added to perform reduction at 50° C. for 2 h; and (8) The liquid, after the reaction, was transferred to a 100 Da dialysis bag, and dialyzed against water for 72 h to remove salts, and the molecular weight and the molecular weight distribution were measured. The results are shown in FIG. 1-c. Then, the fucosylated chondroitin sulfate oligosaccharides having a molecular size concentrated at 6 oligomers to 18 oligomers were intercepted by an ultrafiltration membrane having a pore size of 5 kDa and an ultrafiltration membrane having a pore size of 10 kDa, and lyophilized. The molecular weight and the molecular weight distribution were measured, and the results are shown in FIG. 1-d. A final yield was 1.60%, calculated based on the dried sea cucumber. It only took one week to obtain the oligosaccharides from the sea cucumber raw material. Compared with the traditional cumbersome preparation steps, the time is greatly shortened, the time cost and economic cost required to purify the polysaccharides are saved, and the fucosylated chondroitin sulfate polysaccharides are fully used for degradation, thereby significantly improving the yield of oligosaccharides.

Samples during the process of the present example and the final sample were measured as follows.

(1) Measurements of Molecular Weight and Molecular Weight Distribution

The crude polysaccharide and the hydrazine-treated polysaccharide were dissolved in pure water to prepare a solution (2-5 mg/mL), and measured through a 0.22 μm water film. The measurement conditions were: Waters 1525 equipped with Waters Ultrahydrogel 500 column (7.8×300 mm, Milford, Mass., USA), the mobile phase was 0.2 mol/L sodium chloride solution, the flow rate was 0.5 mL/min, the column temperature and measurement temperature both were 30° C., the detector was Waters 2414, the measurement time was 25 minutes, and a series of dextran standards having known molecular weights was used to detect the molecular weight of the samples.

The sample, after being degraded and intercepted by the ultrafiltration membranes, was dissolved in pure water to prepare a solution (2-5 mg/mL), and measured with a 0.22 μm water film. The measurement conditions were: Waters1525 equipped with Superdex™ Peptide 10/300GL column (10×300 mm, GE, Uppsala, Sweden), the mobile phase was 0.2 mol/L sodium chloride solution, the flow rate was 0.4 mL/min, and the measurement temperature was 30° C., the detector was Waters 2414, and the measurement time was 60 minutes. In the molecular weight distribution diagram, for different components, a ratio of content is reflected by a ratio of area.

Figure 2:
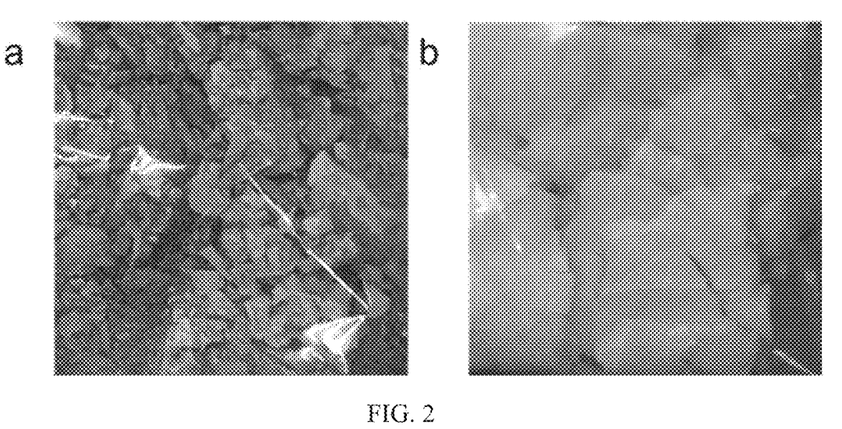
FIG. 2 illustrates appearances of polysaccharide before and after hydrazine treatment: a. crude polysaccharide attached with pigment before hydrazine treatment; b. mixed polysaccharides after hydrazine treatment, in which the pigment is removed by centrifugation.

FIG. 1 illustrates the molecular weight distribution of samples at different stages during the preparation of fucosylated chondroitin sulfate oligosaccharides. It can be seen from FIG. 1-a that two kinds of crude sea cucumber polysaccharides were conveniently and quickly obtained by ultrafiltration. It can be seen from FIG. 1-b and FIG. 2 that the hydrazine treatment partially deacetylates the fucosylated chondroitin sulfate and meanwhile promotes the separation of polysaccharide from pigments, which can be removed by high-speed centrifugation, thereby avoiding the time-consuming, labor- and cost-intensive method of traditional ion exchange purification. Due to strong alkali environment, the hydrazine treatment may lead to different degrees of β elimination of the two polysaccharides and thus causes a decrease of the molecular weight. Among them, the β elimination of fucoidan was not significant, while the β elimination of fucosylated chondroitin sulfate was relatively significant. As shown in FIG. 1-c, the nitrous acid selectively attacks the deacetylated amino group of fucosylated chondroitin sulfate, the adjacent glycosidic bonds break, and thus the fucosylated chondroitin sulfate is degraded into oligosaccharides of trisaccharide repeating units with different degrees of polymerization, concentrated from trisaccharide to 18 oligomers, while the molecular weight of fucoidan is almost unaffected. It can be seen from FIG. 1-d that, after the interception with the ultrafiltration membrane, the macromolecules of fucoidan sulfate and molecules smaller than 6 oligomers are removed, so as to obtain the fucosylated chondroitin sulfate oligosaccharides having a molecular weight concentrated from 6 oligomers to 18 oligomers.

(2) Structure Determination with Nuclear Magnetic Resonance 30 mg of the fucosylated chondroitin sulfate polysaccharide (Native FCS) and the final obtained oligosaccharide (Depolymerized FCS) sample were fully dissolved in 500 μL of $D_2O$, and then lyophilized, the hydrogen atom was fully exchanged three times, and then the mixture was dissolved in 500 μL of $D_2O$ and transferred to an NMR tube, and measured at room temperature by using a Hudson-Bruker SB 600 MHz Spectrometer (Madison, Wis., USA).

Figure 3:
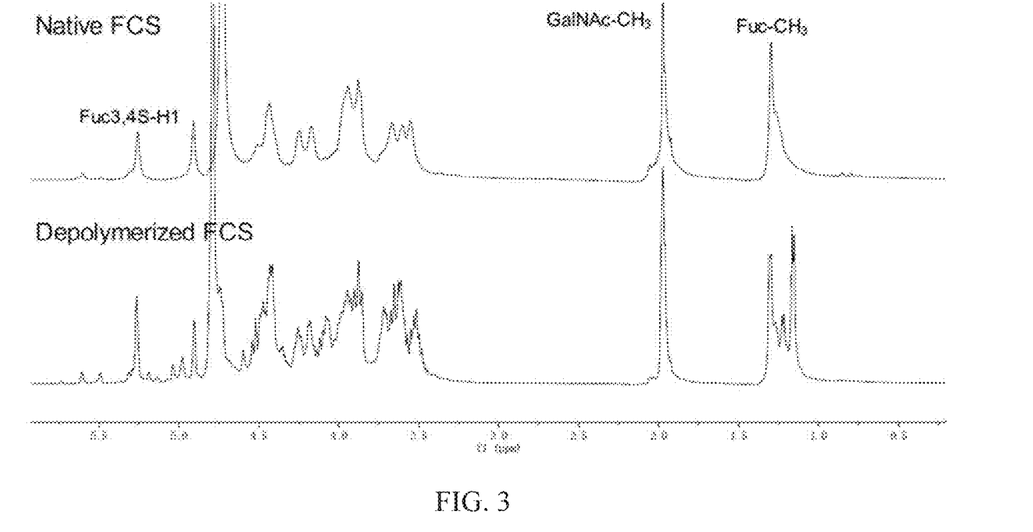
FIG. 3 illustrates a comparison of NMR spectra of fucosylated chondroitin sulfate oligosaccharides and polysaccharide.

FIG. 3 illustrates a comparison of nuclear magnetic resonance spectra of the fucosylated chondroitin sulfate oligosaccharides and polysaccharide. Compared with the original polysaccharide, the structure of the obtained fucosylated chondroitin sulfate oligosaccharides remained basically unchanged, and important active sites such as fucose branch (Fuc-$CH_3$) and sulfated modification (Fuc3, 4S-H1) remained basically unchanged.

(3) Measurement of In Vitro Anticoagulant Activity of Fucosylated Chondroitin Sulfate Oligosaccharides The final obtained fucosylated chondroitin sulfate oligosaccharides (DFCS) were formulated with normal saline into solutions with final concentrations of 8, 16, 32, 64, and 128 μg/mL, the normal saline was used as a blank control, and heparin sodium (UFH) and enoxaparin (LMWH) were used as positive controls.

Human venous blood was added to a plastic tube containing 0.109 mol/L sodium citrate anticoagulant at a ratio of 9:1, mixed gently, and centrifuged at 3000 r/min for 15 min, and the serum was harvested for anticoagulant activity experiments. For APTT assay, 72 μL of plasma and 8 μL of sample solution were mixed and incubated at 37° C. for 1 min, and then 20 μL of APTT test reagent was added to the mixed solution and incubated at 37° C. for 5 min. Finally, 10 μL of calcium chloride solution (0.025 mol/L), which was pre-warmed at 37° C., was added, and at the same time the coagulation time was recorded by an automatic coagulation analyzer. For TT assay, 45 μL of plasma and 5 μL of the sample solution were mixed and incubated at 37° C. for 1 min, and finally 50 μL of T test reagent was added and at the same time the coagulation time was recorded. All coagulation assays were performed 3 times in parallel, and the mean value was calculated. The results were shown as the concentration required to double the coagulation time, and activity unit using heparin sodium (212 IU/mg) as a standard.

A coagulation factor inhibition assay was performed with a 96-well plate. For antithrombin (AT)-mediated anti-FIIa factor assay (anti-FIIa/AT) and anti-FXa factor assay (anti-FXa/AT), 30 μL of the sample solution and 30 μL of 1 IU/mL AT were mixed and incubated at 37° C. for 2 min, then 30 μL of 24 NIH/mL FIIa (or 8 μg/mL of FXa) was added and incubated at 37° C. for 2 min (1 min for FXa), and finally 30 μL of 1.25 mmol/L FIIa chromogenic substrate CS-01 (38) or 1.2 mmol/L FXa chromogenic substrate SXa-11 was added. A change rate in absorbance within 3 min at 405 nm was read to represent FIIa activity and FXa activity. For anti-FXase factor assay (anti-Fxase), 30 μL of the sample, 30 μL of 2 U/mL VIII factor and 30 μL of 60 nmol/L IXa factor (FIIa factor, calcium chloride and phospholipid) were mixed and incubated at 37° C. for 2 min, then 30 μL of 50 nmol/L X factor was added and incubated at 37° C. for 1 min, and finally 30 μL of 8.4 mmol/L FXa chromogenic substrate SXa-11 was added. A change rate of absorbance within 4.5 min at 405 nm was read to represent the FXa activity. All coagulation assays were performed 3 times in parallel to calculate the mean value. The results were shown as half-inhibitory concentration and activity unit using heparin sodium (212 IU/mg) as a standard.

The results of the in vitro anticoagulant activity assays of the fucosylated chondroitin sulfate oligosaccharides are shown in Table 1. It can be seen from Table 1 that the fucosylated chondroitin sulfate oligosaccharides can significantly prolong APTT, i.e., having an activity in significantly inhibiting the intrinsic coagulation pathway, but have no significant effect in prolonging TT, i.e., the mixture of oligosaccharides cannot inhibit the common coagulation pathway. Further, the coagulation factor inhibition assays indicate that the mixed oligosaccharides have relatively weak AT-mediated anti-FIIa activity and anti-FXa activity but significant anti-FXase activity. That is, the mixture of oligosaccharides can selectively inhibit intrinsic FXase activity in the coagulation pathway.

TABLE 1

| Samples      |         | DFCS   | UFH   | LMWH  |
|--------------|---------|--------|-------|-------|
| Mw           | (kDa)   | 3.6    | 18    | 4.5   |
| APTT         | μg/mL   | 112    | 12    | 36.5  |
|              | IU/mg   | 22.7   | 212   | 69.6  |
| TT           | μg/mL   | >128   | 8.81  | 33.1  |
|              | IU/mg   | <14.6  | 212   | 56.4  |
| anti-FIIa/AT | μg/mL   | >1000  | 0.5   | 1.53  |
|              | IU/mg   | <1.00  | 212   | 69.2  |
| anti-Fxa/AT  | μg/mL   | 24     | 0.47  | 0.88  |
|              | IU/mg   | 4.15   | 212   | 113   |
| anti-Fxase   | μg/mL   | 1.17   | 0.36  | 1.39  |
|              | IU/mg   | 65.7   | 212   | 55.4  |

(4) Measurement of In Vivo Antithrombotic Activity and Side Effects of Fucosylated Chondroitin Sulfate Oligosaccharides (4.1) In Vivo Antithrombotic Activity Assay Male SD rats (body weight ranging from 250 g to 300 g) were randomly divided into 4 groups, 8 rats in each group. The final obtained fucosylated chondroitin sulfate oligosaccharides (DFCS) were dissolved in normal saline. As a blank control group, a positive control group, a high dose sample group and a low dose sample group, the rats, at their backs, were respectively injected with normal saline at an amount of 1 mL per kg of body weight, LMWH at an amount of 4 mg per kg of body weight, DFCS at an amount of 10 mg per kg of body weight, and DFCS at an amount of 5 mg per kg of body weight. After about 60 min, the rats were anesthetized with 10% chloral hydrate at an amount of 0.3 mL per 100 g of body weight, and the abdominal cavity was opened to free the inferior vena cava and its branches, and the branches were ligated. 2% tissue thromboplastin was injected through the femoral vein at an amount of 1 mL per kg of body weight. After about 20 seconds, a lower end of the left renal vein was ligated, and the abdominal cavity was closed. After 20 min, the abdominal cavity was re-opened, and the inferior vena cava was longitudinally cut to remove the thrombus. The thrombus was cleaned up and dried at 50° C. for 24 hours, and the thrombus weight was measured. The results were expressed as the mean value plus a standard deviation.

Figure 4:
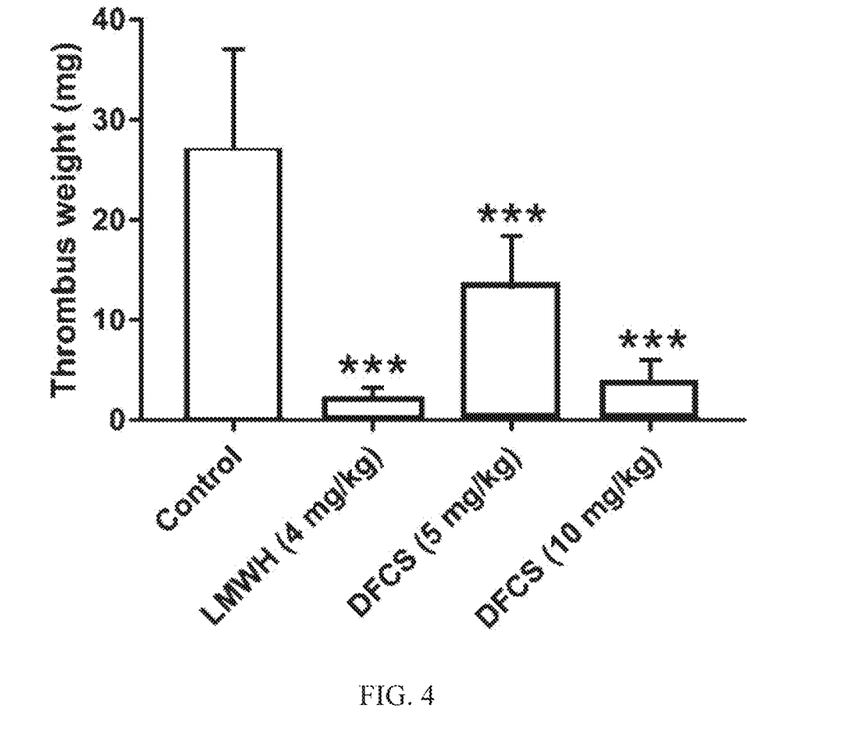
FIG. 4 illustrates in vivo antithrombotic activity of fucosylated chondroitin sulfate oligosaccharides ($P<0.01$, *$P<0.001$ vs. control).

FIG. 4 illustrates the results of in vivo antithrombotic activity of the fucosylated chondroitin sulfate oligosaccharides. The fucosylated chondroitin sulfate oligosaccharides can significantly inhibit deep vein thrombosis in rats, and have a dose-effect, i.e., an inhibition ratio of the high-dose group (10 mg/kg) was 86.4%, which was close to the inhibition effect of the LMWH group (93.1%), and the low-dose group (5 mg/kg) also had a significant antithrombotic effect (50.7%). In combination with the in vitro coagulation factor inhibition assays, it can be inferred that the antithrombotic effect of the fucosylated chondroitin sulfate oligosaccharides is attributed to the inhibition of intrinsic FXase activity, which hinders the production of Fxa, and slows the coagulation process.

(4.2) Bleeding Side Effect Test

Kunming mice (body weight ranging from 18 g to 22 g) were randomly divided into 3 groups, 6 mice in each group. The final obtained fucosylated chondroitin sulfate oligosaccharides (DFCS) were dissolved in normal saline. As a blank control group, a positive control group, and a sample group, the mice, at their backs, were subcutaneously injected with normal saline, LMWH at an amount of 40 mg per kg of body weight, and DFCS at an amount of 120 mg per kg of body weight, respectively. After about 60 min, 5 mm of the tails of the mice were cut and immersed in 40 mL of pure water, stirred for 90 min in a 37° C. water bath. The absorbance at 540 nm was read and the blood loss was calculated by means of the standard curve. The results were expressed as the mean value plus a standard deviation.

Figure 5:
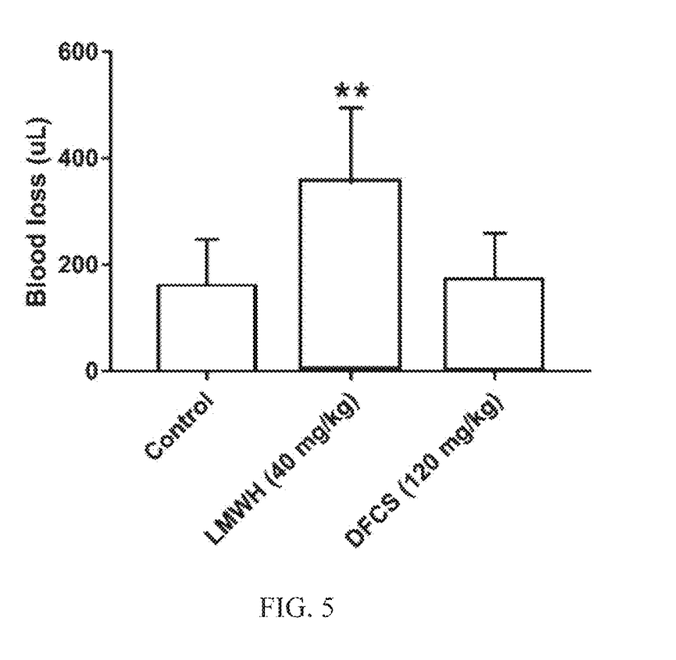
FIG. 5 illustrates a bleeding test of fucosylated chondroitin sulfate oligosaccharides (**$P<0.01$ vs. control).

FIG. 5 illustrates the results of the bleeding side effect test of the fucosylated chondroitin sulfate oligosaccharides. The mice had no risk of bleeding after being subcutaneously administered with the fucosylated chondroitin sulfate oligosaccharides at a dose of 120 mg per kg of body weight, while the mice had significant bleeding after being subcutaneously administered with LMWH at a dose of 40 mg per kg of body weight. This indicates that the obtained fucosylated chondroitin sulfate oligosaccharides can avoid the risk of bleeding, while exerting anticoagulant and antithrombotic effects, which is attributed to their selective inhibition of intrinsic FXase. Therefore, it is safer than LMWH.

(4.3) Blood Pressure and Heart Rate Tests after Intravenous Injection

The final obtained fucosylated chondroitin sulfate oligosaccharides (DFCS) and polysaccharide (FCS) were dissolved in normal saline to prepare a 10 mg/mL solution. Male SD rats (body weight about 200 g) were randomly divided into 2 groups, 8 rats in each group. The rats were anesthetized with chloral hydrate, the carotid artery was separated to expose about 10 mm of blood vessel. A distal end of the blood vessel was ligated with a surgical wire and a proximal end was clamped with an arterial clamp. Then, a small opening was cut in the blood vessel with scissors, a cannula connected to a blood pressure signal meter was inserted, and ligated. After 10 min adaptation, DFCS was injected at a dose of 10 mg per kg of body weight in the tail vein, as a sample group, and FCS was injected at a dose of 5 mg per kg of body weight in the tail vein, as a control group. The changes in blood pressure were recorded, and the mean arterial pressure and heart rate were calculated based on the blood pressure signals.

Figure 6:
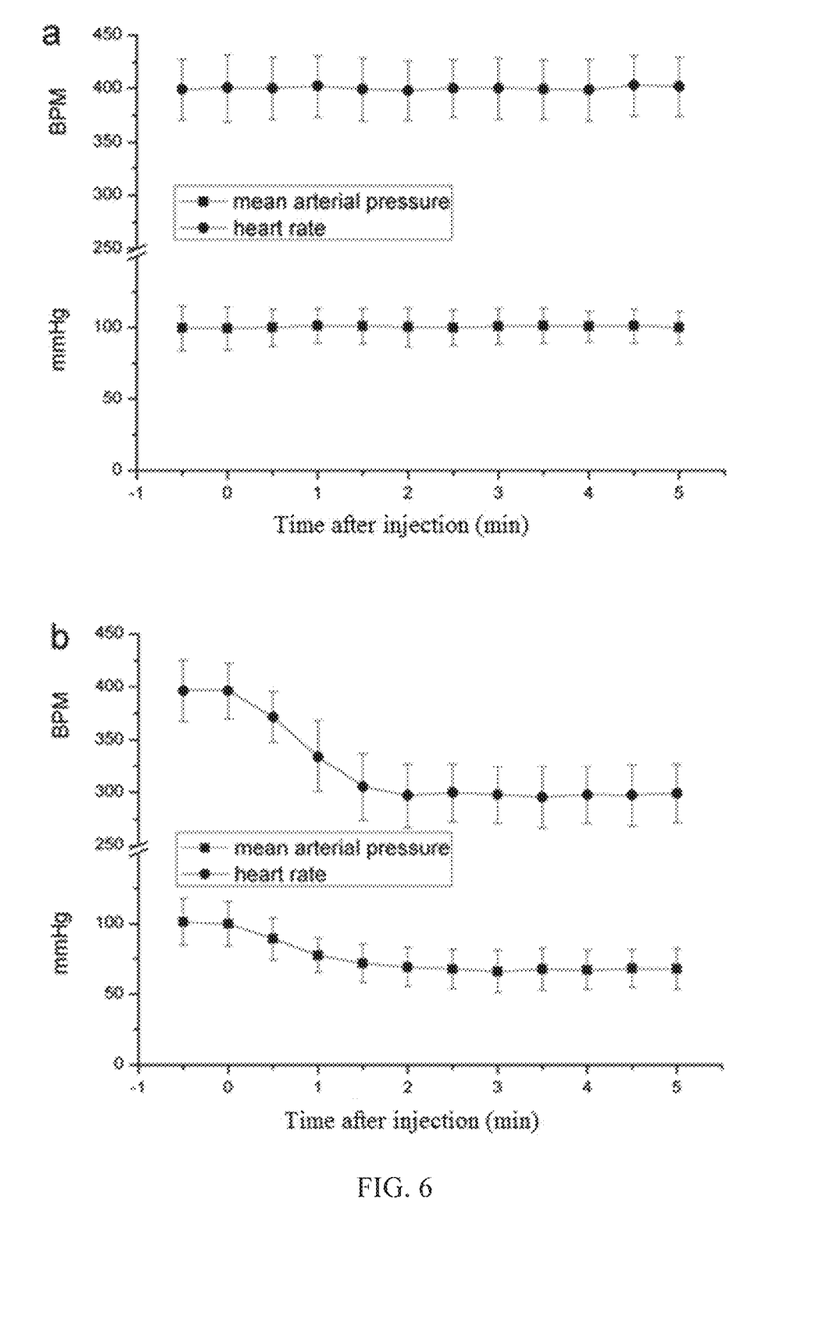
FIG. 6 illustrates a blood pressure and heart rate test after intravenous injection of fucosylated chondroitin sulfate oligosaccharides.

FIG. 6 illustrates the results of the blood pressure and heart rate tests after the intravenous injection of the fucosylated chondroitin sulfate oligosaccharides. After the administration with the fucosylated chondroitin sulfate oligosaccharides at a dose of 10 mg per kg of body weight in the tail vein, the mean arterial pressure and heart rate of rats remained stable and the same as those before the administration, as shown in FIG. 6-a. However, after an administration with the fucosylated chondroitin sulfate polysaccharides at a dose of 5 mg per kg of body weight in the tail vein, the mean arterial pressure and heart rate of rats started to decrease after the administration, and after about 1.5 min, stabilized, as shown in FIG. 6-b. The fucosylated chondroitin sulfate polysaccharides can cause the activation of XIIa factor in the blood, which leads to the release of a large amount of kallikrein, thereby resulting in hypotension and the decrease of the heart rate or even shock. It can be seen that the obtained fucosylated chondroitin sulfate oligosaccharides can avoid the side effects of hypotension that may be caused by polysaccharide, and thus is safer when exerting the anticoagulant and antithrombotic effects.

Example 2

(1) 100 g of dry powder of *Isostichopus badionotus* was uniformly mixed with 1 L of acetic acid-sodium acetate buffer (0.15 mol/L; pH 7), and the temperature was raised to 70° C., 5 g of papain was added and mixed uniformly to perform enzymolysis for 24 h, and then the mixture was boiled to inactive the enzyme;

(2) The crude polysaccharide was enriched by using a 50 kDa ultrafiltration membrane, washed with pure water until the permeate was colorless, and then lyophilized;

(3) 5 g of the crude polysaccharide was sufficiently dissolved in 25 mL of hydrazine hydrate and 25 mg of hydrazine sulfate was added to react at 60° C. for 24 h, so as to obtain a reaction solution;

(4) Absolute ethanol and saturated saline were added in the reaction solution and centrifuged, and the precipitate was taken and dissolved in water;

(5) After repeating the above operation 4 times, the precipitate was dissolved in water and dialyzed against water with a 500 Da dialysis bag for 72 h;

(6) The dialyzed crude polysaccharide solution was appropriately concentrated and centrifuged at 10000 rpm, the supernatant was harvested and lyophilized, and then 1 g of the lyophilized polysaccharide was taken and dissolved in pure water to prepare a solution (20 mg/mL), which was then kept in an ice bath for later use;

(7) 5.5 mol/L sodium nitrite solution and 0.5 mol/L sulfuric acid were mixed in a volume ratio of 5:4 to obtain a nitrous acid solution which was then kept in the ice bath, then 50 mL of the nitrous acid solution was taken, mixed with 50 mL of the polysaccharide solution and reacted in an ice bath for 10 min, then 0.5 mol/L sodium hydroxide solution was added until the reaction solution was neutral to terminate the reaction, and then 3 mL of 150 mg/mL sodium borohydride solution was rapidly added to perform reduction at 50° C. for 2 h;

(8) The liquid, after the reaction, was transferred to a 500 Da dialysis bag, and dialyzed against water for 48 h to remove salts, and the fucosylated chondroitin sulfate oligosaccharides having a molecular size concentrated from 6 oligomers to 18 oligomers was intercepted with an ultrafiltration membrane having a pore size of 5 kDa and an ultrafiltration membrane having a pore size of 10 kDa and lyophilized, where the final yield was 1.85% calculated based on the dried sea cucumber.

In the present example, it also took only one week to obtain the oligosaccharides from another kind of sea cucumber raw material. The time cost and economic cost, which are required to purify the polysaccharide in the traditional preparation of fucosylated chondroitin sulfate oligosaccharides, are saved, and the fucosylated chondroitin sulfate polysaccharide is fully utilized for degradation, thereby significantly improving the yield of oligosaccharides. The fucosylated chondroitin sulfate oligosaccharides obtained in the present example have an average molecular weight of 3600 Da, and 90% of total components has a molecular weight between 1800 Da to 5400 Da and is trisaccharide-repeating units of varying degrees. The results of nuclear magnetic resonance indicated that, compared with polysaccharide, the sulfated fucose branches did not fall off significantly, i.e., the active sites were well retained. The in vitro anticoagulant activity assay indicated that the anti-IIa factor and anti-Xa factor activities were weak but the anti-Xase factor activity was significant. The in vivo antithrombotic assay and the side effect assay indicated that the fucosylated chondroitin sulfate oligosaccharides have significant in vivo antithrombotic activity, and have no side effects of bleeding and hypotension. The test methods involved in this example are the same as those in Example 1.

Example 3

(1) 100 g of dry powder of *Pearsonothuria graeffei* was uniformly mixed with 2 L of phosphate buffer (0.1 mol/L; pH 8), the temperature was raised to 37° C., 10 g of trypsin was added and mixed uniformly to perform enzymolysis for 10 h, and then the mixture was boiled to inactive the enzyme;

(2) The crude polysaccharide was enriched by using a 5 kDa ultrafiltration membrane, washed with pure water until the permeate was colorless, and then lyophilized;

(3) 5 g of the crude polysaccharide was sufficiently dissolved in 50 mL of hydrazine hydrate and 50 mg of hydrazine hydrochloride was added to react at 90° C. for 12 h, so as to obtain a reaction solution;

(4) Absolute ethanol and saturated saline were added to the reaction solution and centrifuged, and the precipitate was taken and dissolved in water;

(5) After repeating the above operation 4 times, the precipitate was dissolved in water and dialyzed against water with an 8000 Da dialysis bag for 24 h;

(6) The dialyzed crude polysaccharide solution was appropriately concentrated and centrifuged at 6000 rpm, the supernatant was harvest and lyophilized, and then 1 g of the lyophilized polysaccharide was taken and dissolved in pure water to prepare a solution (25 mg/mL), which was then kept in an ice bath for later use;

(7) 5 mol/L sodium nitrite solution and 0.5 mol/L sulfuric acid were mixed in a volume ratio of 3:1 to obtain a nitrous acid solution which was then kept in the ice bath, 50 mL of the nitrous acid solution was taken, mixed with 25 mL of the polysaccharide solution and reacted in an ice bath for 10 min, then 0.3 mol/L sodium hydroxide solution was added until the reaction solution was neutral to terminate the reaction, and then 3 mL of 100 mg/mL sodium borohydride solution was rapidly added to perform reduction at 40° C. for 4 h; and (8) The liquid, after the reaction, was transferred to a 1000 Da dialysis bag, and dialyzed against water for 36 h to remove salts, and the fucosylated chondroitin sulfate oligosaccharides having a molecular size concentrated from 6 oligomers to 18 oligomers were intercepted with an ultrafiltration membrane having a pore size of 3 kDa and an ultrafiltration membrane having a pore size of 8 kDa and lyophilized, where the final yield was 1.70% calculated based on the dried sea cucumber.

In the present example, it took one week to prepare the fucosylated chondroitin sulfate oligosaccharides having the molecular size concentrated from 6 oligomers to 18 oligomers from the sea cucumber raw material. The time cost and economic cost, which are required to purify the polysaccharide in the traditional preparation of fucosylated chondroitin sulfate oligosaccharides, are also saved, and the fucosylated chondroitin sulfate polysaccharide is fully utilized for degradation, thereby significantly improving the yield of oligosaccharides. The fucosylated chondroitin sulfate oligosaccharides obtained in the present example have an average molecular weight of 2700 Da, and 90% of total components has a molecular weight between 1800 Da to 5400 Da and is trisaccharide-repeating units of varying degrees. The results of nuclear magnetic resonance indicated that, compared with polysaccharide, the sulfated fucose branches did not fall off significantly, i.e., the active sites were well retained. The in vitro anticoagulant activity assay showed significant effect in prolonging APTT but insignificant effect in prolonging TT. The test methods involved in this example are the same as those in Example 1.

Example 4

(1) 100 g of *Isostichopus badionotus* was soaked and pulped, then mixed with 2 L of citrate buffer (0.1 mol/L; pH 6), and the temperature was raised to 55° C., 10 g of bromelain was added and mixed uniformly to perform enzymolysis for 30 h, and then the mixture was boiled to inactive the enzyme;

(2) The crude polysaccharide was enriched by using a 60 kDa ultrafiltration membrane, washed with pure water until the permeate was colorless, and then lyophilized;

(3) 5 g of the crude polysaccharide was taken and sufficiently dissolved in 50 mL of hydrazine hydrate and 50 mg of hydrazine hydrochloride was added to react at 95° C. for 18 h, so as to obtain a reaction solution;

(4) Absolute ethanol and saturated saline were added and centrifuged, and the precipitate was taken and dissolved in water;

(5) After repeating the above operation 5 times, the precipitate was dissolved in water and dialyzed against water with a 5000 Da dialysis bag for 24 h;

(6) The dialyzed crude polysaccharide solution was appropriately concentrated and centrifuged at 6000 rpm, the supernatant was harvested and lyophilized, and then 1 g of the lyophilized polysaccharide was taken and dissolved in pure water to prepare a solution (40 mg/mL), which was then kept in an ice bath for later use;

(7) 4 mol/L sodium nitrite solution and 0.5 mol/L sulfuric acid were mixed in a volume ratio of 4:1 to obtain a nitrous acid solution which was then kept in an ice bath, 25 mL of the nitrous acid solution was taken, mixed with 25 mL of the polysaccharide solution and reacted in an ice bath for 20 min, then 0.1 mol/L sodium hydroxide solution was added until the reaction solution was neutral to terminate the reaction, and then 2 mL of 100 mg/mL sodium borohydride solution was rapidly added to perform reduction at 50° C. for 4 h; and (8) The liquid, after the reaction, was transferred to a 500 Da dialysis bag, and dialyzed against water for 36 h to remove salts, and the fucosylated chondroitin sulfate oligosaccharides having a molecular size concentrated from 6 oligomers to 18 oligomers were intercepted with an ultrafiltration membrane having a pore size of 3 kDa and an ultrafiltration membrane having a pore size of 10 kDa and lyophilized, where the final yield was 1.40% calculated based on the dried sea cucumber.

In the present example, it similarly took one week to prepare the fucosylated chondroitin sulfate oligosaccharides having the molecular size concentrated from 6 oligomers to 18 oligomers from the sea cucumber raw material. The hydrazine treatment has effects of decoloration of the crude polysaccharide and partial deacetylation of fucosylated chondroitin sulfate, which avoids the loss during purification of fucosylated chondroitin sulfate and greatly improves the yield of oligosaccharides. The fucosylated chondroitin sulfate oligosaccharides obtained in the present example have an average molecular weight of 2700-3600 Da, and 70% of total components has a molecular weight of 1800 Da to 5400 Da and is trisaccharide-repeating units of varying degrees. The results of nuclear magnetic resonance indicated that, compared with polysaccharide, the sulfated fucose branches of the fucosylated chondroitin sulfate oligosaccharides did not fall off significantly. The in vitro anticoagulant activity assay indicated that the anti-IIa activity of the fucosylated chondroitin sulfate oligosaccharides was smaller than 1 IU/mg, the anti Xa activity was 4.52 IU/mg, and anti-Xase activity was 56.8 IU/mg. The test methods involved in this example are the same as those in Example 1.

Example 5

(1) 100 g of *Thelenota ananas* was soaked and pulped, then uniformly mixed with 2 L of acetic-sodium acetate buffer (0.1 mol/L; pH 6), and the temperature was raised to 60° C., 10 g of papain was added and mixed uniformly to perform enzymolysis for 18 h, and then the mixture was boiled to inactive the enzyme;

(2) The crude polysaccharide was enriched by using a 50 kDa ultrafiltration membrane, washed with pure water until the permeate was colorless, and then lyophilized;

(3) 5 g of the crude polysaccharide was taken and sufficiently dissolved in 50 mL of hydrazine hydrate and 50 mg of hydrazine sulfate was added to react at 90° C. for 12 h, so as to obtain a reaction solution;

(4) Absolute ethanol and saturated saline were added and centrifuged, and the precipitate was taken and dissolved in water;

(5) After repeating the above operation 4 times, the precipitate was dissolved in water and dialyzed against water with a 3500 Da dialysis bag for 48 h;

(6) The dialyzed crude polysaccharide solution was appropriately concentrated and centrifuged at 8000 rpm, the supernatant was harvested and lyophilized, and then 1 g of the lyophilized polysaccharide was taken and dissolved in pure water to prepare a solution (40 mg/mL), which was then kept in an ice bath for later use;

(7) 5 mol/L sodium nitrite solution and 0.5 mol/L sulfuric acid were mixed in a volume ratio of 5:2 to obtain a nitrous acid solution, which was then kept in an ice bath, 25 mL of the nitrous acid solution was taken, mixed with 25 mL of the polysaccharide solution and reacted in an ice bath for 30 min, then 0.1 mol/L sodium hydroxide solution was added until the reaction solution was neutral to terminate the reaction, and then 2 mL of 100 mg/mL sodium borohydride solution was rapidly added to perform reduction at 50° C. for 4 h; and (8) The liquid, after the reaction, was transferred to a 1000 Da dialysis bag, and dialyzed against water for 24 h to remove salts, and the fucosylated chondroitin sulfate oligosaccharides having a molecular size concentrated from 6 oligomers to 18 oligomers were intercepted with an ultrafiltration membrane having a pore size of 5 kDa and an ultrafiltration membrane having a pore size of 10 kDa and lyophilized, where the final yield was 1.68% calculated based on the dried sea cucumber.

In the present example, experiments were performed on *Thelenota ananas*, it also took one week to prepare the fucosylated chondroitin sulfate oligosaccharides having the molecular size concentrated from 6 oligomers to 18 oligomers from the sea cucumber raw material. The hydrazine treatment has effects of decoloration of crude polysaccharide and partial deacetylation of fucosylated chondroitin sulfate, which greatly enhances the yield of and efficiency of the preparation of high-purity oligosaccharides. The fucosylated chondroitin sulfate oligosaccharides obtained in the present example have an average molecular weight of 3600 Da, and 80% of total components has a molecular weight of 1800 Da to 5400 Da and is trisaccharide-repeating units of varying degrees. The results of nuclear magnetic resonance indicated that, compared with polysaccharide, the sulfated fucose branches of the fucosylated chondroitin sulfate oligosaccharides did not fall off significantly. The animal experiments showed that the fucosylated chondroitin sulfate oligosaccharides can significantly inhibit deep vein thrombosis in rats, and have a dose-effect, i.e., the inhibition ratio of the high-dose group (10 mg/kg) was 89.5%, which was close to the inhibition effect of the LMWH group (93.1%), and the low-dose group (5 mg/kg) also had a significant antithrombotic effect (56.8%). In addition, the oligosaccharides did not cause the side effects of bleeding and hypotension. The test methods involved in this example are the same as those in Example 1.

It should be understood that the above are a few specific examples of the present invention. Apparently, the present invention is not limited to the above examples, and may have many other variations. All variations that can be directly derived or conceived by those skilled in the art from the disclosed contents of the present invention shall fall within the protection scope of the present invention.

What is claimed is:

1. A method for rapidly producing fucosylated chondroitin sulfate oligosaccharides, comprising the following steps:
   (1) pulverizing sea cucumber, mixing the pulverized sea cucumber, protease and a buffer solution having a pH of 5-8 according to a solid-liquid ratio of 1 g:(0.05-0.15) g:(10-30) mL for enzymolysis, and then boiling to inactivate enzyme, so as to obtain an enzymatic hydrolysate;
   (2) intercepting the enzymatic hydrolysate obtained in step (1) with an ultrafiltration membrane to obtain a crude polysaccharide concentrate solution, subjecting the crude polysaccharide concentrate solution to repeated diluting with water and concentrating by intercepting with an ultrafiltration membrane until a permeate is colorless, and then lyophilizing the concentrate solution to obtain crude polysaccharide;

(3) uniformly mixing the crude polysaccharide obtained in step (2) and hydrazine hydrate at a ratio of 1 g:(5-20) mL, adding a catalyst for catalyzing a deacetylation effect of the hydrazine hydrate on fucosylated chondroitin sulfate in the crude polysaccharide, reacting at 60-105° C. for 6-24 h, to obtain a reaction solution;

(4) adding absolute ethanol, and adding saturated saline dropwise until the crude polysaccharide precipitates, harvesting a precipitate after centrifuging, re-dissolving the precipitate into water to obtain a crude polysaccharide solution;

(5) repeating step (4), and transferring a crude polysaccharide solution obtained after repeating step (4) more than twice to a dialysis bag to remove residual ethanol and hydrazine by dialysis;

(6) centrifuging the dialyzed crude polysaccharide solution in step (5) to separate pigment impurities from polysaccharide, lyophilizing a supernatant containing the polysaccharide, and then dissolving the lyophilized polysaccharide in pure water to obtain a polysaccharide solution for later use;

(7) mixing an ice-bathed nitrous acid solution with the polysaccharide solution obtained in step (6), reacting in an ice bath for 10-60 min, then adding a sodium hydroxide solution until the reaction solution is neutral to terminate the reaction, and adding a sodium borohydride solution for reduction; and (8) transferring a product obtained in step (7) to a dialysis bag to remove residual salts by dialysis, and then intercepting fucosylated chondroitin sulfate oligosaccharides with an ultrafiltration membrane, to obtain components having a molecular weight smaller than 6000 Da.

2. The method according to claim 1, wherein, in step (1), the protease is papain, and the buffer solution is an acetic acid-sodium acetate buffer solution having a concentration of 0.05-0.15 mol/L, and the solid-liquid ratio is 1 g:(0.08-0.12) g:(15-25) mL, a temperature of the enzymolysis is 50-70° C., and a duration of the enzymolysis is 12-24 h.

3. The method according to claim 1, wherein the ultrafiltration membrane used in step (2) has a pore size of 10-50 kDa.

4. The method according to claim 1, wherein, in step (3), the crude polysaccharide and the hydrazine hydrate are uniformly mixed at a ratio of 1 g:(8-12) mL, the added catalyst is hydrazine sulfate or hydrazine hydrochloride, a reacting temperature is 90-105° C., and a reacting duration is 8-18 h.

5. The method according to claim 1, wherein the dialysis bag used in step (5) has a molecular pore size of 500-3500 Da.

6. The method according to claim 1, wherein, in step (6), a rotation speed of the centrifuging is 8000 rpm or greater.

7. The method according to claim 1, wherein, in step (7), the nitrous acid solution is prepared by mixing a 5.5 mol/L sodium nitrite solution with 0.5 mol/L sulfuric acid in a volume ratio of 5:(2-4), the sodium hydroxide solution has a concentration of 0.5 mol/L, the sodium borohydride solution has a concentration of 150 mg/mL, and the reduction is performed at 50° C. for 2 h.

8. The method according to claim 1, wherein, in step (8), the dialysis bag has a pore size of 100-500 Da, and the fucosylated chondroitin sulfate oligosaccharides are intercepted with an ultrafiltration membrane having a pore size of 5 kDa and an ultrafiltration membrane having a pore size of 10 kDa.

* * * * *